United States Statutory Invention Registration [19]

Chi

[11] Reg. Number: H365

[43] Published: Nov. 3, 1987

[54] NEW ENERGETIC POLYMER, P-DEND

[75] Inventor: Minn-Shong Chi, Newark, Del.

[73] Assignee: The United States of America as represented by the Secretary of the Army, Washington, D.C.

[21] Appl. No.: 8,511

[22] Filed: Jan. 29, 1987

[51] Int. Cl.[4] ..... C07C 101/26; C08G 69/44

[52] U.S. Cl. ..... 560/169; 528/291

[56] References Cited

PUBLICATIONS

Hackh's Chemical Dictionary, Fourth Edition, (Copyright 1969), p. 428.

*Primary Examiner*—John F. Terapane
*Assistant Examiner*—Eric Jorgensen
*Attorney, Agent, or Firm*—John C. Garvin, Jr.; Freddie M. Bush

[57] ABSTRACT

Poly(diethylene glycol-4,7-dinitrazadecane-dioate), P-DEND), is synthesized by the Michael addition of ethylene dinitramine to methyl acrylate to yield the intermediate compound dimethyl-4,7-dinitrazadecane-dioate (DMDND). DMDND is reacted for a period of about 18 hours with diethylene glycol (DEG) at about 85° C. in presence of a p-toluenesulfonic acid catalyst to yield P-DEND. The product (P-DEND) is purified by passing it through a silica gel column using methylene chloride as solvent. The average molecular weight of P-DEND ranges from about 1500–2000. P-DEND is shown to be compatible with stabilized nitroglycerin for use as an energetic polymer binder for high performance propellants.

2 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

NEW ENERGETIC POLYMER, P-DEND

DEDICATORY CLAUSE

The invention described herein was made in the course of or under a contract or subcontract thereunder with the Government; therefore, the invention described herein may be manufactured, used and licensed by or for the government for governmental purposes without the payment to me of any royalties thereon.

BACKGROUND OF THE INVENTION

Solid propellant binders which employ inert polymers yield a lower specific impulse as compared with solid propellant binders which employ energetic binders. Examples of inert or nonenergetic polymers are polyglycol adipate (PGA), polyethylene glycol (PEG), and polycaprolactone (PCL). Thus, the replacement of inert polymers by energetic polymers will improve the performance in both tactical and strategic propellants while maintaining good mechanical properties and processability.

An alternate consideration for achieving high performance propellants for future tactical and strategic systems includes obtaining high performance by employing high solids of oxidizers such as cyclotetramethylenetetranitramine (HMX) or cyclotrimethylenetrinitramine (RDX) and/or high content of high energy plasticizers such as nitroglycerine (NG). This alternate approach particularly, which involves high solids of HMX or RDX and increasing the high energy plasticizer content leads to other changes such as degradation of mechanical properties and processability and changes to shock sensitivity which makes the approach of improving performance by replacing of inert polymers (PGA or PEG) with energetic polymers a more desirable approach to increasing specific impulse. Energetic polymers which are compatible with nitroglycerin is an additional, attractive benefit.

Therefore, an object of this invention is to provide a method for synthesis of an energetic polymer for use in nitrate ester plasticized propellants.

Another object of this invention is to provide a method for synthesis of an energetic polymer which is very compatible with nitroglycerin.

SUMMARY OF THE INVENTION

The energetic polymer, poly(diethylene glycol-4,7-dinitrazadecane-dioate) (P-DEND), is synthesized in a two-step process. The first synthesis step is the Michael addition of ethylene dinitramine to methyl acrylate to yield the intermediate compound dimethyl-4,7-dinitrazadecane-dioate (DMDND). Polymer formation is achieved by the reaction of DMDND with diethylene glycol (DEG) using an elevated temperature and a catalyst of p-toluenesulfonic acid.

A 15:1 mole ratio of DEG to DMDND is reacted at 85° C. for 18 hours, under vacuum, to remove the methanol which is generated. After the excess DEG is removed by high vacuum distillation, the mother liquid is further heated at 80° C., under high vacuum, so that polymerization proceeds. The product is subsequently purified by passing it through a silica gel column using methylene chloride as solvent. The average molecular weight of P-DEND obtained by this method ranges from 1500–2000.

DESCRIPTION OF THE PREFERRED EMBODIMENT

Poly(diethylene glycol-4,7-dinitrazadecane-dioate) (P-DEND), is synthesized by the Michael addition of ethylene dinitramine to methyl acrylate to yield the intermediate compound dimethyl-4,7-dinitrazadecane-dioate (DMDND). Polymer formation is achieved by the reaction of DMDND with diethylene glycol (DEG) using an elevated temperature and a catalyst of p-toluenesulfonic acid.

A mole ratio of 15 of DEG to 1 of DMDND is preferred for polymer formation wherein the reaction is first achieved at 85° C. for about 18 hours and under vacuum conditions to remove the methanol which is generated. Excess DEG is then removed by high vacuum distillation. The liquid product remaining is further heated at 80° C., under high vacuum, so that polymerization proceeds.

The product (P-DEND) is purified by passing it through a silica gel column using methylene chloride as solvent. The average molecular weight of the purified product ranges from about 1500–2000.

COMPATIBILITY TESTS OF ENERGETIC POLYMER WITH NG

The P-DEND is very compatible with nitroglycerin (NG), which is used as a plasticizer in high energy propellants. In gas generation tests (at 70° C.), as shown in Table I, the total pressure of gas generated in three weeks time, for the mixture of P-DEND with NG is comparable to that generated by NG (99/1) alone. This test, which has been performed several times, demonstrates that purified P-DEND is compatible with NG. In a binder mechanical property study, as shown in Table II, the tensile strengths of P-DEND binder and PGA binder (inert polymer control binder) are the same, while the P-DEND binder has higher modulus and lower elongation. The higher modulus for the P-DEND binder is attributed to the shorter chain length and resultant higher crosslink density than the PGA binder. The equivalent weights of P-DEND (X443-62) and PGA (S1011-35) are 846 and 1480, respectively. These tests indicate, therefore, that P-DEND will perform as an energetic binder for high energy propellants having a good service life and good mechanical properties.

TABLE I

P-DEND GASSING STUDY AT 70° C.

| Sample | P-DEND M. Wt. | Weight Ratio | Total Pressure (mmHg/g) Aging Time 1 Week | 2 Weeks | 3 Weeks |
|---|---|---|---|---|---|
| (1) P-DEND (78-2)/NG (99/1)* | 1900 | 20/80 | 1.23 | 2.11 | 2.66 |
| (2) P-DEND (85-2)/NG (99/1) | 1500 | 20/80 | 1.83 | 1.94 | 2.55 |
| (3) NG(99/1) alone | — | 100 | 1.96 | 2.71 | 3.13 |

*NG(99/1) = nitroglycerin 99 parts and 1 part stabilizer

TABLE II

BINDER MECHANICAL PROPERTIES

| Prepolymer | Eq Wt. | Pl/Po | NCO/OH | Mechanical Properties-* $E_o$ (psi) | $\sigma$ (psi) | $\epsilon$ (%) |
|---|---|---|---|---|---|---|
| P-DEND (X443-62) | 846 | 2.5 | 1.0 | 39 | 10.3 | 31 |

TABLE II-continued

| BINDER MECHANICAL PROPERTIES | | | | | | |
|---|---|---|---|---|---|---|
| | Eq | | | Mechanical Properties-* | | |
| Prepolymer | Wt. | Pl/Po | NCO/OH | $E_o$ (psi) | $\sigma$ (psi) | $\epsilon$ (%) |
| PGA (S1011-35) | 1480 | 2.5 | 1.0 | 19 | 10.5 | 86 |

*77° F., 1.0 in/in/min

I claim:

1. A method for preparing poly(diethylene glycol-4,7-dinitrazadecane-dioate) comprising:

(i) completing a Michael addition of ethylene dinitramine to methyl acrylate to yield dimethyl-4,7-dinitrazadecane-dioate (DMDND);

(ii) reacting under vacuum, said DMDND with an excess ratio amount of diethylene glycol to said DMDND at an elevated temperature of about 85° C. while employing a catalyst of p-toluenesulfonic acid to form diethylene glycol-4,7-dinitrazadecane-dioate in mother liquid, said vacuum effecting removal of methanol as generated during said reacting;

(iii) continuing said reacting for about 18 hours under vacuum and thereafter initiating and completing a high vacuum distillation process to remove excess diethylene glycol from mother liquid containing said diethylene glycol-4,7-dinitrazadecane-dioate;

(iv) heating said mother liquid remaining after said distillation of excess diethylene glycol under high vacuum at about 80° C. to achieve polymerization of said diethylene glycol-4,7-dinitrazadecane-dioate to form poly(diethylene glycol-4,7-dinitrazadecane-dioate) (P-DEND); and, (v) purifying said P-DEND by passing it through a silica gel column using methylene chloride as solvent to yield pure P-DEND having a molecular weight ranging from about 1500 to about 2000.

2. The method of claim 1 for preparing poly(diethylene glycol-4,7-dinitrazadecane-dioate) wherein said excess ratio of said diethylene glycol to said DMDND is about 15:1.

* * * * *